US010860689B1

(12) United States Patent
Whitaker et al.

(10) Patent No.: US 10,860,689 B1
(45) Date of Patent: Dec. 8, 2020

(54) AUTOMATIC MEDICATION PRESCRIPTION PROCESSING AND PROFILE MANAGEMENT FOR PERSONS UNDER LEGAL GUARDIANSHIP BASED ON TRANSMITTED DIGITAL IMAGES

(71) Applicant: WALGREEN CO., Deerfield, IL (US)

(72) Inventors: Lindsey Whitaker, Chicago, IL (US); Kevin David Meyer, Deerfield, IL (US)

(73) Assignee: WALGREEN CO., Deerfield, IL (US)

( * ) Notice: Subject to any disclaimer, the term of this patent is extended or adjusted under 35 U.S.C. 154(b) by 421 days.

(21) Appl. No.: 15/695,743

(22) Filed: Sep. 5, 2017

(51) Int. Cl.
*G06Q 50/00* (2012.01)
*G06F 19/00* (2018.01)
*G06Q 50/24* (2012.01)
*G16H 40/63* (2018.01)

(52) U.S. Cl.
CPC ......... *G06F 19/3456* (2013.01); *G06Q 50/24* (2013.01); *G16H 40/63* (2018.01)

(58) Field of Classification Search
CPC .......... G06Q 50/00; G06F 19/00; G06F 17/60
USPC ........................................................ 705/2, 3
See application file for complete search history.

(56) References Cited

U.S. PATENT DOCUMENTS

| | | | | |
|---|---|---|---|---|
| 5,845,255 A | * | 12/1998 | Mayaud | G06F 19/3456 705/3 |
| 6,240,394 B1 | * | 5/2001 | Uecker | G06Q 10/10 705/3 |
| 8,626,530 B1 | * | 1/2014 | Tran | G06Q 50/22 705/2 |
| 2011/0125528 A1 | * | 5/2011 | Padate | G16H 10/60 705/3 |
| 2014/0100874 A1 | * | 4/2014 | Wood | G06F 19/00 705/3 |
| 2015/0149203 A1 | * | 5/2015 | Csurka | G06Q 10/1095 705/3 |
| 2015/0339460 A1 | * | 11/2015 | Marsico | G06F 19/3456 705/2 |

OTHER PUBLICATIONS

Google patents search, Jan. 21, 2020 (Year: 2020).*
Google patents search, Jul. 10, 2020 (Year: 2020).*
IP.com search, Jul. 10, 2020 (Year: 2020).*

* cited by examiner

*Primary Examiner* — Dilek B Cobanoglu
(74) *Attorney, Agent, or Firm* — Marshall, Gerstein & Borun LLP; Randall G. Rueth

(57) ABSTRACT

A system for associating a person under the legal guardianship of a user with a profile of the user for managing and refilling medications is disclosed. An electronic device of the user captures a digital image of medication information of the person under the user's legal guardianship. Visual identifiers in the medication information encode information regarding the person such as medication information. The electronic device may transmit a request on behalf of the user to associate the person under the user's legal guardianship with a profile of the user for managing medications and other requests on behalf of the person under the user's legal guardianship.

20 Claims, 9 Drawing Sheets

AUTOMATIC MEDICATION PRESCRIPTION PROCESSING AND PROFILE MANAGEMENT FOR PERSONS UNDER LEGAL GUARDIANSHIP BASED ON TRANSMITTED DIGITAL IMAGES

BACKGROUND

Parents or guardians with minor children under their legal guardianship and care often must fill and refill prescriptions for medication for the minor child at a pharmacy. Management and processing of prescription medication and refills of prescription medication held by the minor child can be complicated because the process of submitting a prescription request to a pharmacy may require information regarding the prescription itself, personal information regarding the minor child, the minor's child health insurance, pharmacy registration status, etc. Parents and guardians are often unable to efficiently complete the submission of a prescription refill request for a prescription held by a minor child under the parent of guardian's care.

SUMMARY OF THE DISCLOSURE

This summary is provided to introduce a selection of concepts in a simplified form that are further described in the Detailed Descriptions. This summary is not intended to identify key features or essential features of the claimed subject matter, nor is it intended to be used to limit the scope of the claimed subject matter.

In an implementation, a method for processing medication refills. The method may include receiving at a server, an electronic message originating from an electronic device of a user, the electronic message comprising a digital image of medication information, detecting, by a computer processor, a set of visual identifiers depicted in the digital image of medication information, the visual identifiers encoding information regarding a person, determining, based on the set of visual identifiers, that the person is a minor child, receiving a response from the user, the response indicating user instructions to associated the minor child with the profile of the user.

DETAILED DESCRIPTIONS

Authorized medical practitioners may issue prescriptions for prescription medication to patients under their care who are legally minor children. It is often the duty of a parent or guardian caring for the minor child to fill and/or refill the medication at a pharmacy to provide medical care to the minor child and to manage the minor child's medications at the pharmacy.

Figure 1:
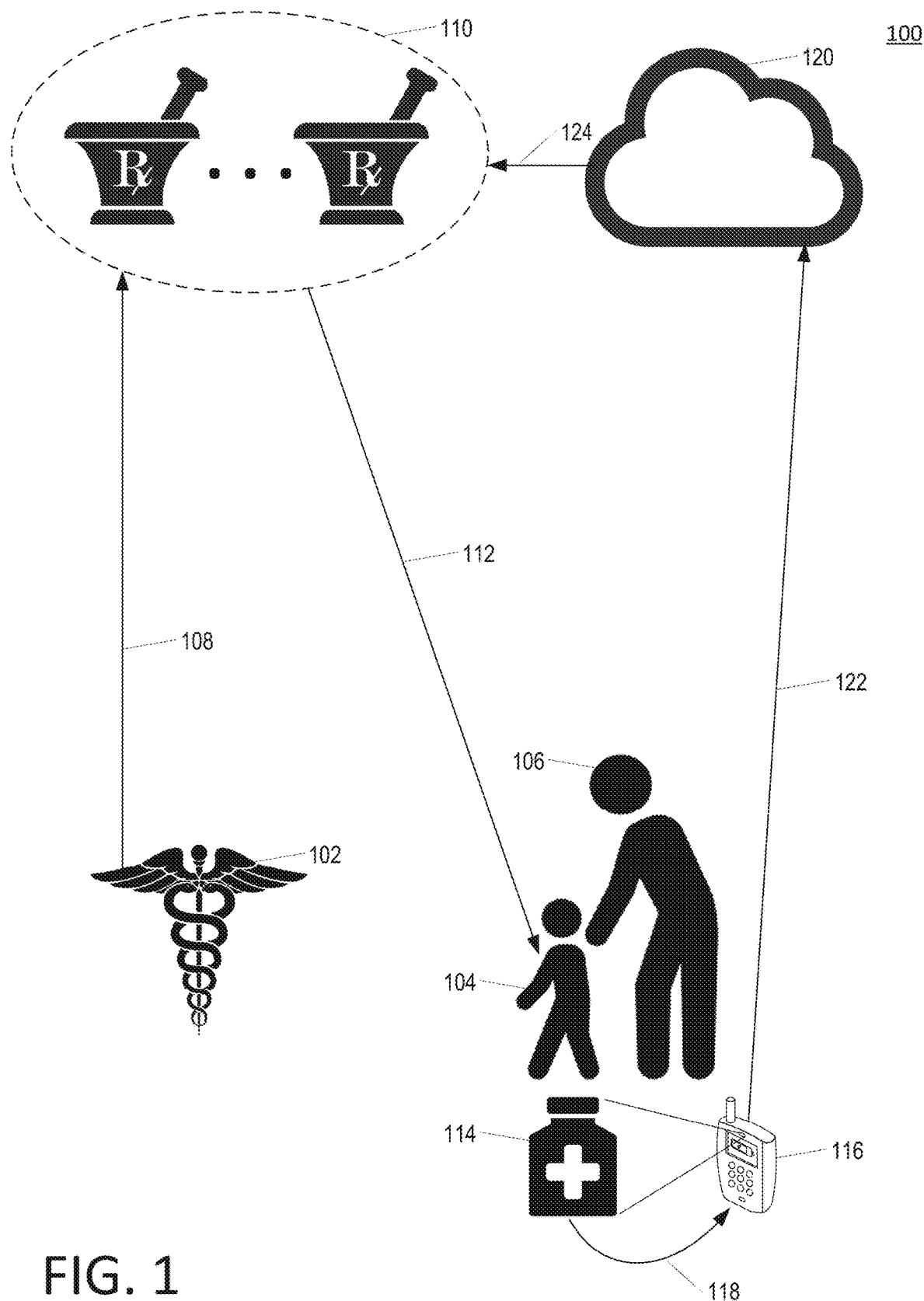
FIG. 1 is a schematic diagram of an example system for automatic prescription processing and pharmacy profile management for minor children based on transmitted digital images.

FIG. 1 is a schematic diagram of an example system 100 for automatic prescription medication processing and pharmacy profile management for minor children based on transmitted digital images. When an authorized medical professional 102 issues (or "writes") a medical prescription for a person who is a minor child 104, a parent or legal guardian 106 of the minor child is responsible for managing, filling, and/or refilling the prescription on behalf of the minor child 104. The age requirements of a minor child vary by legal jurisdiction. As used herein, the term "minor child" refers to any individual who is under the legal care of another person. A minor child may be under the legal care of a parent/guardian 106, as described in the example system 100, and may also include persons who are not children, but are under the legal care of another person due to incapacity, mental handicap, or for other reasons applicable in various legal jurisdictions in which one or more retail pharmacy locations of a pharmacy network 110 dispense prescription medication.

When the medical professional 102 issues a prescription for medication for the minor child person 104, the medical professional 102 transmits a prescription request (108) to a pharmacy. The pharmacy may be an individual pharmacy or it may be a pharmacy network such as pharmacy network 110 illustrated in the example illustrated in FIG. 1. If the pharmacy is a pharmacy network, the medical professional 102 may designate a particular retail location in the pharmacy network 110 to dispense the prescription medication. The parent/guardian 106 may then visit the designated retail pharmacy location in the network of retail pharmacy locations 110 to obtain the medical prescription on behalf of the minor child 104 (112).

When the parent/guardian 106 obtains a prescription medication on behalf of a minor child 104, the prescription medication may be enclosed in one or more prescription medication containers 114. The one or more prescription medication containers 114 may include without limitation bags, pill containers, trays, vials, bottles, boxes, etc. The containers 114 may include printed or otherwise embedded information (e.g., in a barcode, human-readable text, electronic chip, RFID tag, etc.). Examples of information included in the prescription medication container 114 also includes without limitation information identifying the pharmacy or the pharmacy network 110 (e.g., a pharmacy's name, contact information, address, etc.), instructions on opening the container 114, personal information regarding the minor child 104 (e.g., name, home address, age, etc.), information regarding the issuing medical professional 102 (e.g., the issuing medical professional's name, hospital, contact information, etc.), information regarding the prescription medication (e.g., type of medication, pill count, refill count, instructions regarding taking the medication, a prescription identification number, etc.).

Some prescriptions include one or more "refills" of the prescription medication contained therein (e.g., a "refill count"). A refill indicates that the person holding the prescription is entitled to return to the pharmacy to receive more of the medication as many times as the refill count indicates. For example, a prescription may include 50 pills with a refill count of 2. A person holding this prescription would therefore be entitled to return to the pharmacy two times to obtain another bottle of 50 pills after the person has consumed the first 50 pills. One way a parent/guardian 106 may be made aware of the number of refills associated with a particular prescription is when a refill count is printed on the container 114. When a person 104 or a parent/guardian 106 requests a refill of a medical prescription for which one or more refills are remaining, a pharmacy in the network of pharmacies 110 may dispense more prescription medication to the person or parent/guardian 106 without obtaining approval from the issuing medical professional 102. After dispensing a refill, the pharmacy in the network of pharmacies 110 decrements (e.g., reduces by one) the number of remaining refills associated with the medical prescription. Another way a parent/guardian 106 may be made aware of a refill count for a prescription medication issued to a minor child 104 under the parent/guardian's care is to access an on-line profile associated with a pharmacy or the pharmacy network 110 to view remaining refills on prescriptions held by the minor child 104.

The network of pharmacies 110 may track remaining prescription refills for a person electronically (e.g., for providing information to a parent/guardian 106 regarding prescriptions and prescription refills via an on-line profile). In one implementation, the network of pharmacies 110 maintains a user database with user profiles owned by or associated with the persons to whom the pharmacies in the network of pharmacies have dispensed prescription medications. The one or more user databases may contain information regarding persons including without limitation biographical information of the person (e.g., the person's address, phone number, e-mail address, age, gender, etc.), billing information (e.g., credit card information, other payment information, etc.), insurance information (e.g., the person's insurance carrier, insurance policy identification number, etc.), and/or historical information (e.g., medical prescriptions that the person has filled in the past at the pharmacy or has requested to be transferred from another pharmacy, names of physicians who have issued prescriptions to the person in the past, etc.). Users (e.g., the parent/guardian 106) may log into a user interface to view and/or modify the user profile associated therewith to monitor remaining prescription medication refills, request refills, etc.

One type of information that may be stored in a pharmacy user database is an association between a patient and another person. An example of an association between a patient and another person is an association between a minor child 104 and the minor child's parent/guardian 106. An association between the minor child 104 and the minor child's parent/guardian 106 may indicate to pharmacy locations in the pharmacy network 110 that the parent/guardian 106 is authorized to obtain and manage prescriptions for prescription medication at the pharmacies in the network of pharmacies 110 on behalf of the minor child 104. If the parent/guardian 106 requests a medical prescription refill of a prescription held by the minor child 104 from a pharmacy in the network of pharmacies 110, the pharmacy may dispense the refill based on a determination that the parent/guardian 106 and the minor child are associated the user database of the pharmacy network 110 (e.g., the minor child has been added to, or associated with, a profile of the parent/guardian).

Authorizing a parent/guardian 106 to obtain a medical prescription refill on behalf of a minor child 104 based on an association between the parent/guardian 106 and the minor child 104 in the user data of a pharmacy network 110 may be done if such as association between the parent/guardian 106 and minor child 104 exists in the user database. To initiate an association between the parent/guardian 106 and the minor child 104 in the user database, the parent/guardian 106 may use an electronic device 116 to capture a digital image of the container 114 at line 118 to electronically obtain information identifying the minor child 104. The parent/guardian 106 may then transmit the information identifying the minor child 104 to the network of pharmacy locations 110 using the electronic device 116 via the communications network 120 (122 and 124). One way of electronically obtaining information identifying the minor child 104 from the container 114 is to use a camera on the electronic device 116 to capture a digital image of the information on the surface of the container 114. Other ways of obtaining information identifying the minor child 104 from the container 114 is to use a wireless communication (e.g., near-field communication (NFC), radio-frequency ID tag (RFID), etc.) Once the electronic device 116 has captured the information identifying the minor child 104 from the container 114, the electronic device 116 may transmit the digital image to the network of pharmacies 110 for analysis and extraction of the information identifying the minor child 104. Alternatively, or additionally, the electronic device 116 may analyze and extract the information identifying the minor child 104 itself and transmit the information to the network of pharmacies 110 without including a digital image of the surface of the container 114.

The electronic device 116 may be any type of electronic device such as a mobile device (e.g., a smartphone, tablet, etc.), notebook computer, GPS (Global Positioning System) or GPS-enabled device, wearable electronic device, PDA (personal digital assistant), pager, computing device configured for wireless communication, etc. The pharmacies in the network of pharmacies 110 may include a respective set of computers, terminals, and/or server(s) located at the pharmacies or associated therewith that may support a checkout procedure or a point of sale. In particular, the parent/guardian 106 may purchase products or services from any of the pharmacies in the network of pharmacies 110 thought the use of the computers, terminals, and/or server(s) associated therewith. The electronic device 116 may communicate with the pharmacies in the network of pharmacies 110 and the computers, terminals, and/or servers associated therewith via one or more networks 120. In some implementations, the network 120 may support any type of data communication via a technology standard or communications protocol (e.g., GSM, CDMA, TDMA, ECDMA, LTE, EDGE, OFDM, GPRS, EV-DO, UWB, Internet, IEEE 802, WiMax, Wi-Fi, Bluetooth, etc.).

When the parent/guardian 106 transmits information identifying the minor child 104 to the network of pharmacies 110 via the communications network 120, the transmission may be accompanied by instructions to associate the minor child 104 with a profile belonging to the parent/guardian in a user database of the pharmacy network 110. If the pharmacy network 110 approves a request to associate the minor child 104 with a profile belonging to the parent/guardian 106 in the user database of the pharmacy network 110, then the pharmacy network 110 will be able to approve any future medical prescription refill requests made by the parent/guardian 106 for a medical prescription belonging to the minor child 104 based on the association between the parent/guardian and the minor child 104 in the user database. The network of pharmacies 110 may require the parent/guardian 106 to validate information regarding the minor child and/or provide evidence that the parent/guardian is authorized to request prescription medication refills on behalf of the minor child 104.

Capturing the information identifying the minor child 104 from the container 114 therefore provides an efficient and convenient way for the parent/guardian 106 to request an association between the parent/guardian and the minor child 104 in the pharmacy network 110's user database. Accepting such an association request in this manner reduces costs to the pharmacy network 110 in managing, filling, and/or refilling medical prescriptions on behalf of a minor child 104 under the care and supervision of the parent/guardian 106. For example, once an association has been created between the parent/guardian and the minor child 104 in the user database of the pharmacy network 110, then the parent/guardian 106 need not obtain and scan/capture information from a medical prescription container 114 to request medical prescription refills in the future from the network of pharmacies 110 on behalf of the minor child 104. Instead, the parent/guardian 106 will be able to request the medical prescription refill directly from the network of pharmacies 110 on behalf of the minor child 104 because the user database of the pharmacy network 110 will show an association between the parent/guardian 106 and the minor child 104, and thus will show that the parent/guardian 106 is approved to request medical prescription refills on behalf of the minor child 104. Accepting a request to associate the minor child 104 with a profile of the parent/guardian 106 also reduces costs to the parent/guardian 106 because it reduces the information the parent/guardian 106 must produce in order to make a prescription medication refill request on behalf of the minor child 104 and reduces transaction time and cost for the parent/guardian 106 in managing prescriptions held by the minor child 104.

Figure 2:
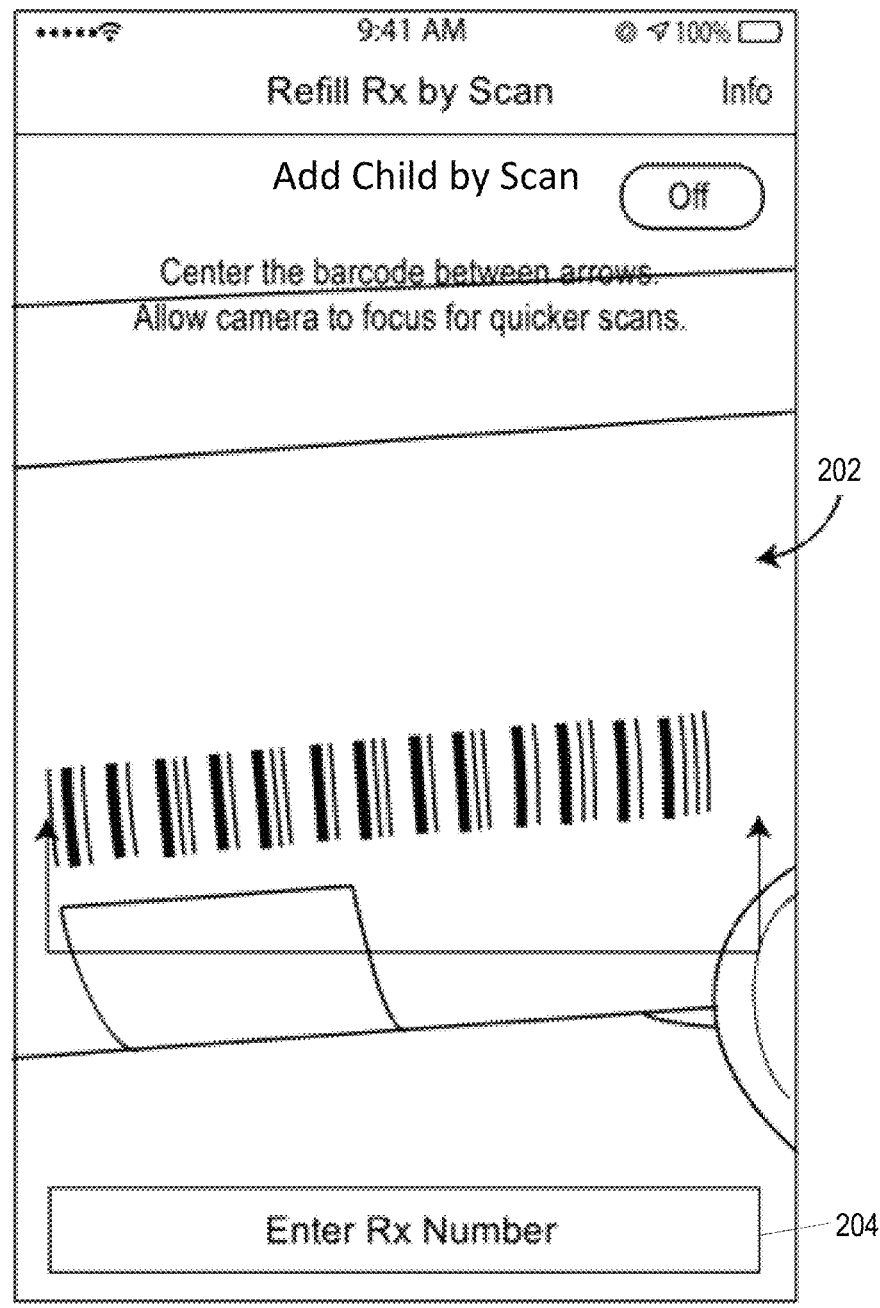
FIG. 2 is an example user interface screen associated with a system for automatic medication processing and pharmacy profile management for minor children based on transmitted digital images.

FIG. 2 is an example user interface screen 200 associated with a system for automatic prescription processing and pharmacy profile management for minor children based on transmitted digital images. The user interface screen 200 may be displayed by an electronic device operated by a parent/guardian via a user interface as part of an application executing on the electronic device. The user interface may enable the user to make various selections and display corresponding interface screens accordingly. The exemplary interface screens depict various functionalities associated with a request to associate a minor child with a profile at a network of pharmacies owned by a parent/guardian.

The interface screen 200 includes a "live view" of image data captured by an image sensor of an electronic device associated with a parent/guardian. In operation, the image sensor of the electronic device is configured to capture an identification of a prescription (e.g., a barcode associated with the prescription, text information printed on a prescription container or bag, a prescription label, or other prescription identifications). The interface screen 200 may instruct the user to position the identification/barcode so that it is detectable by the image sensor (as shown: "Center the barcode between arrows. Allow camera to focus for quicker scans.").

The image sensor may be configured to automatically detect a barcode, such as when the barcode is positioned between the arrows or box portion 202 of the interface screen 200. In particular, the electronic device may continuously analyze the image data detected by the image sensor to determine whether the image data indicates a barcode. In at least one implementation, the user may select a manual input selection 204 which enables the user to manually input a prescription number or other identification of the prescription via the user interface. Throughout this disclosure, the term "barcode" should be understood to be generic and inclusive of all types of machine-readable data representation. Barcodes could be, for example, conventional rectangular segment barcodes as well as two dimensional QR codes or matrix barcodes. Most QR codes have black modules arranged in a square pattern on a white background. Smaller version may be referred to as micro QR codes and design QR codes include a picture or logo to enhance conversion rates.

In some implementations, an application executing on the electronic device may interpret a captured barcode image to generate prescription data (e.g., a prescription number, a number of refills, etc.) and transmit the prescription data to a server associated with a network of pharmacies. In other implementations, an application executing on the electronic device may transmit the barcode image itself to a server associated with a network of pharmacies, which may interpret the barcode image to obtain prescription data. In at least one implementation, the application executing on the electronic device may transmit the barcode image to a third-parts server or third-party application (e.g., an application API) which may interpret the barcode image to obtain prescription data and transmit the obtained prescription data to a server associated with the network of pharmacies. After receiving a barcode image or prescription data associated with the a prescription obtained from interpreting a barcode image, a server associated with the network of pharmacies may identify any prescription refill information associated with the prescription and transmit the prescription refill information associated with the prescription refill to the electronic device. In another implementation, an application executing on the electronic device may also transmit a device and/or user identification to a server associated with the network of pharmacies (e.g., a user and/or device identification associated with a user profile owned by the user of the electronic device, a user and/or device identification automatically detected by the application executing on the electronic device, a user and/or device identification manually entered by the user, etc.). The application executing on the electronic device may transmit the device and/or user identification at any point in facilitating the request to associated a minor child with a profile owned by the user.

Figure 3:
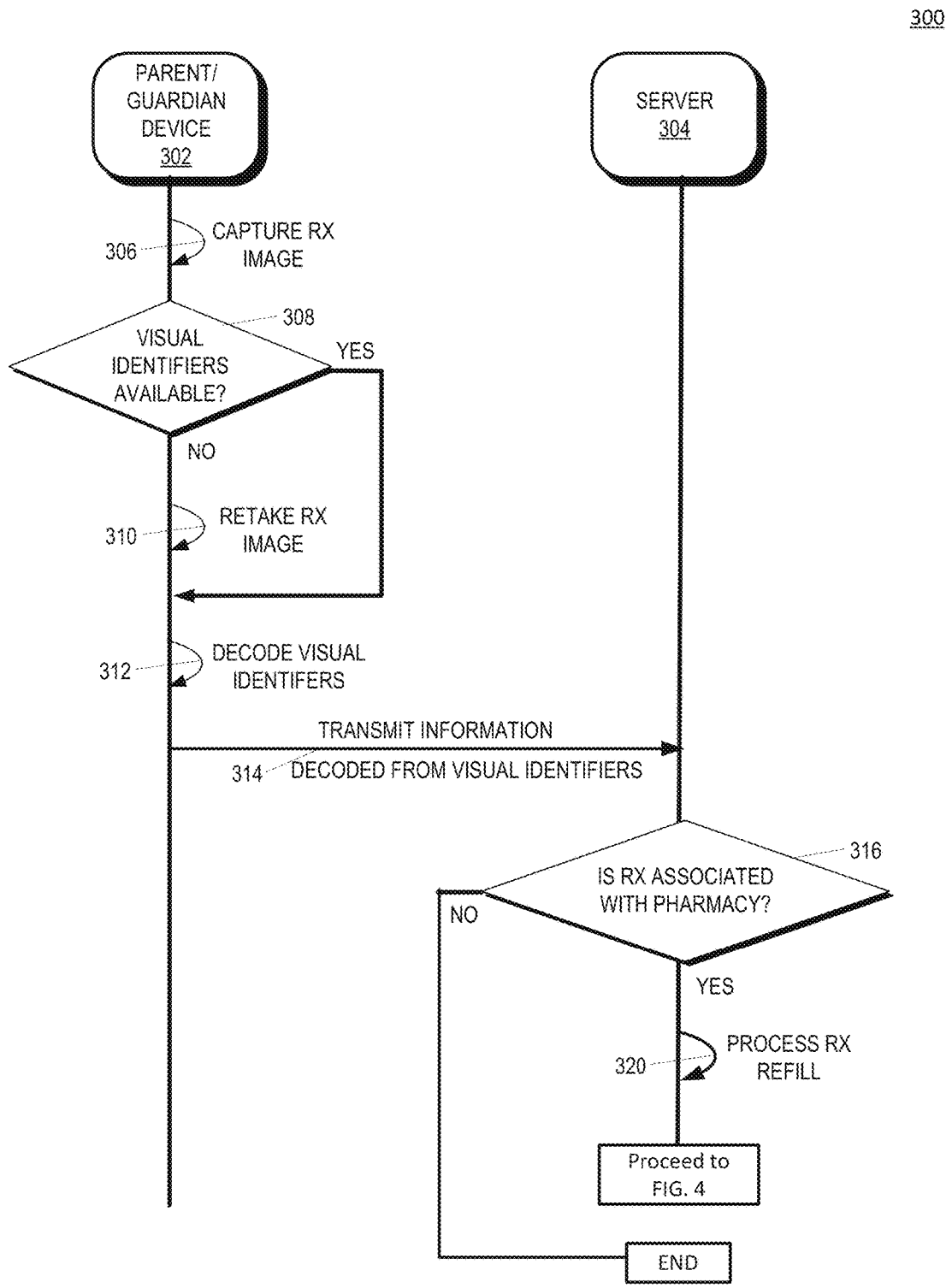
FIG. 3 is an example signal diagram associated with a system for automatic prescription processing and profile management for minor children based on transmitted digital images.

FIG. 3 is an example signal diagram 300 associated with a system for automatic prescription processing and pharmacy profile management for minor children based on transmitted digital images. The signal diagram 300 includes a parent/guardian electronic device 302 that may be operated by the parent/guardian of a minor child person, such as the electronic device disclosed with respect to FIG. 1, and a server 304. The server 304 may include one or more databases (e.g., a prescription information database, a user database, etc.). The server 304 may constitute a set of back-end components that are remote from the parent/guardian electronic device 302, where the set of back-end components may be associated with a pharmacy network having a set of retail locations. In another implementation, the server 304 may be associated with a single pharmacy retail location or with a third-party that does not directly operate any pharmacy locations.

The signal diagram 300 begins when a parent/guardian uses the electronic device 302 to capture (306) one or more digital images of prescription medication information. In particular, the parent/guardian may use the electronic device 302 to capture digital image(s) of prescription medication information such as a container associated with the prescription medication (e.g., a vial, box, tray, pill bottle, etc.). In one implementation, the container associated with a prescription medication includes a set of visual identifiers such as one or more graphical objects, logos, text, barcodes, labels, etc. The prescription medication container may include a label presenting various information associated with the prescription, including but not limited to information associated with the minor child (e.g., name, address, phone number, birthdate, etc.), dosage and usage information, and refill information. In an implementation, the parent/guardian electronic device 302 may prompt, via a user interface, the parent/guardian to capture certain portions or angles of the container. In some implementations, the parent/guardian electronic device 302 may receive or access the digital images from another device or component of the system as an alternative to directly capturing the digital image(s).

After capturing or otherwise accessing the digital image(s), the parent/guardian device determines (308) whether visual identifiers are accessible in the digital image. Visual identifiers may not be accessible to the parent/guardian device 302 due to low image quality or incomplete capture of the visual identifiers in the digital image. In some implementations, the parent/guardian device 302 may employ one or more digital image analysis techniques, algorithms, routines, etc. to determine whether the visual identifiers encode prescription medication information, such as prescription medication information displayed on a prescription medication container. The parent/guardian device 302 may also employ digital image analysis techniques, algorithms, routines, etc. to assess and consider image characteristics such as sharpness, noise, range, tone reproduction, contrast, color accuracy, distortion, vignetting, exposure accuracy, lateral chromatic aberration (LCA), lens flare, color moire, and/or artifacts in the digital image(s).

At 308, the parent/guardian device 302 may analyze the digital image(s) to identify a set of visual identifiers that may be depicted in the digital image(s), such as one or more graphical objects, logo, text, barcodes, labels, etc. The parent/guardian device 302 may employ any type of image analysis technique, including an object recognition technique to analyze the digital image(s).

One type of visual identifier is a unique logo for a pharmacy (e.g., position thereof, label shape/size, and color pattern for prescription medication containers used to dispense prescription medication from the pharmacy). In at least one implementation, a pharmacy associated with server 304 may include certain visual identifiers on prescription medication containers that may be uniquely associated with the pharmacy. In analyzing the visual identifiers in the digital image(s) in (308), the parent/guardian device 302 may determine whether any identified visual identifiers match or are similar to the visual identifiers for the pharmacy associated with the server 304. In particular, the parent/guardian device 302 may compare the identified visual identifier(s) to the visual identifier(s) for the pharmacy, where the parent/guardian device 302 may calculate a similarity score based on the comparison and deem that the visual identifier(s) is a "match" if the calculated similarity score satisfied a match condition. For example, if the parent/guardian device 302 calculated a similarity score of 85% and the match condition is satisfied by a similarity score of 75% or higher, then the server 304 may deem that the visual identifier(s) in the digital image(s) match those associated with the pharmacy. It should be appreciated that in comparing the visual identifier(s), the server 304 may employ any type of algorithm, calculation, and/or technique to determine whether the match condition is satisfied.

In analyzing the visual identifiers, the parent/guardian device 302 may extract information encoded in the visual identifiers in the digital images(s). One type of information encoded in the visual identifiers in the digital image(s) is biographical information regarding the person to whom the prescription medication in the container was issued (e.g., name, address, phone number, birthdate, etc.). In at least one implementation, the container includes redundant encoding of biographical information regarding the person (e.g., human-readable text information printed on the label of the container and information encoded in a barcode printed on the container).

If visual identifiers are not accessible in the digital image (e.g., the information contained in the visual identifiers is not decodable), the parent/guardian device 302 may request that the parent guardian retake the digital image of the prescription medication information. If visual identifiers are accessible in the digital image (308), the parent/guardian device 302 decodes the visual identifiers to extract the information contained therein regarding the person associated with the prescription. A transmitting operation 314 transmits the information decoded from the visual identifiers to the server 304. In another implementation, the parent/guardian device 302 may transmit the digital images of the prescription medication information itself to the server 304 via a network connection for the server 304 to decode the information in the visual identifiers. In some implementations, the parent/guardian device 302 may execute an application into which the parent/guardian may select the captured digital image(s) (e.g., from a camera roll) as well as information for the destination. For example, the application executing on the electronic device of the parent/guardian that may support SMS/MMS message transmission (e.g., the digital image(s) are sent as part of an MMS message).

In some implementations, the destination identification may identify the component or entity to which the digital image(s) are to be sent. For example, the destination may be a mobile station international subscriber directory number (MSISDN) associated with the server 304. As another example, the destination identification may be a short code associated with the server 304, in which case the digital image(s) may be routed to a short code message server, which may forward the digital image(s) to the server 304. In other implementations, other destination identifications are envisioned (e.g., telephone number, email address, website URL, etc.). In the example illustrated in FIG. 3, the destination identification is the server 304.

At 316, the server 304 may determine whether the prescription medication information depicted in the digital image(s) is associated with a pharmacy. More particularly, if the analysis in 316 results in the visual identifier(s) depicted in the digital image(s) matching the visual identifiers associated with the pharmacy, then the server 304 may deem that the container of the prescription medication depicted in the digital image(s) is associated with the pharmacy ("YES") and processing may proceed to (320). In contrast, if the analysis in (316) results in the visual identifiers depicted in the digital images(s) not matching the visual identifiers associated with the pharmacy, then the server 304 may deem that the container depicted in the digital image(s) is associated with another pharmacy ("NO"), and processing may proceed to the end or the pharmacy may request a transfer of the prescription from another pharmacy.

At 320, the server 304 may initiate processing associated with facilitating a refill for the prescription. In particular, the server 304 may determine or identify details or information associated with the prescription depicted in the digital image(s) and/or information transmitted to the server 304 in operation 314 such as without limitation a prescription number, patient information (e.g., name, address, phone number, birthdate, etc.). In determining or identifying the details or information, the server 304 may perform one or more optical character recognition (OCR) techniques. In one implementation, the server 304 may perform an OCR technique on a barcode that may be depicted in the digital image(s), where the output of the OCR technique may indicate certain details associated with the prescription (e.g., prescription number, patient information, etc.).

The server 304 may receive prescription refill instructions from the parent/guardian device 302. In particular, the server 304 may query the parent/guardian device 302 to confirm refill instructions as well as the retail location for the refill. The parent/guardian may use the device 302 to confirm the prescription refill and the retain location for the refill. The server 304 may accordingly process (320) the prescription refill according to the specified information. In particular, the server 304 may transmit an instruction to the specified retail location to cause the prescription to be refilled at the specified retail location. Thus, the parent/guardian is able to pick up the prescription refill at the specified retail location and processing of signal diagram 400 may end. After processing the prescription refill (320), the signal diagram 300 may proceed to the signal diagram of FIG. 4.

Figure 4:
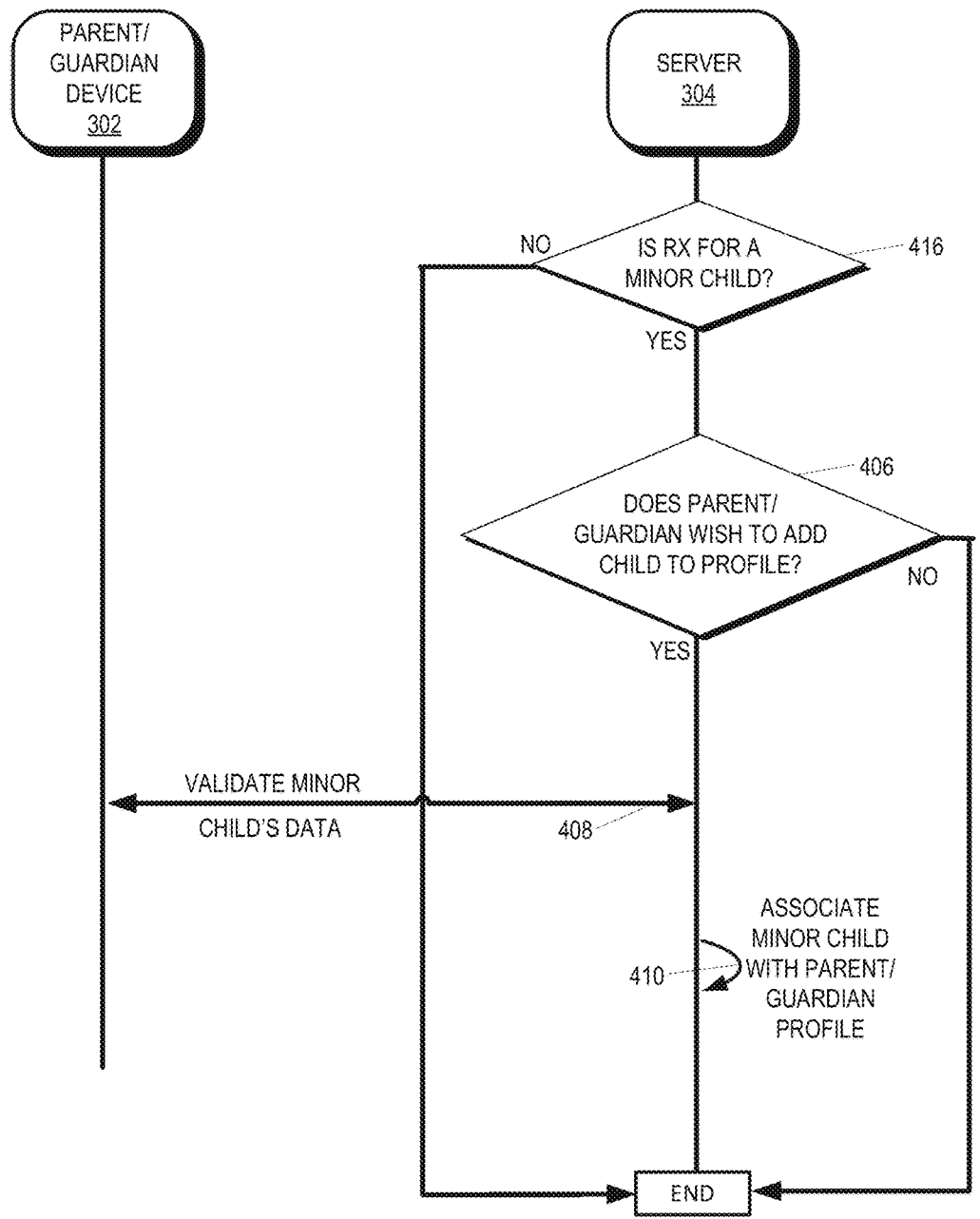
FIG. 4 is another example signal diagram associated with a system for automatic prescription processing and pharmacy profile management for minor children based on transmitted digital images.

FIG. 4 is another example signal diagram 400 associated with a system for automatic prescription processing and pharmacy profile management for minor children based on transmitted digital images. Signal diagram 400 begins by determining whether the prescription medication information is a prescription for a minor child. The server 304 may calculate an age of the person to whom the prescription medication in the container was issued (316) based on a birthdate encoded in the visual identifiers. If the server determines that the person is not a minor child ("NO"), then the operations 400 end. If the server determines that the person is a minor child ("YES"), then the operations 400 proceed to operation. In at least one implementation, the server 304 does not base a determination of whether the person is a minor child (416) on the person's age. Instead the server 304 may base a determination of whether the person is a minor child on another indicia in the visual identifiers, for example without limitation, and express indication in the person's biographical information that the person is a minor child or otherwise under the legal supervision of another person.

After a determination by the server 304 that a person identified by visual identifiers on a prescription medication container is a minor child or otherwise under the legal supervision of another person (416) based on visual identifiers in a digital image of a prescription medication container, the server 304 determines whether the minor child is already associated with a profile of the parent/guardian in a user database associated with the server 304. The server 304 may determine whether the minor child is already associated with the parent/guardian by searching, querying, etc. the user database (e.g., an entry in the user database corresponding to the parent/guardian may have one or more fields indicating other profiles that are associated therewith, etc.).

The server 304 determines the identity of the parent/guardian based on an identification transmission received from the parent/guardian device 302. In at least one implementation, the parent/guardian may have created a user profile at an earlier time and logged into an app executing on the parent/guardian device with a username and password. A user profile in this way may include profile information relating to the parent/guardian that can be used to uniquely identify the parent/guardian (e.g., first name, last name, address, insurance policy number, social security number, state identification number, driver's license number, etc.). In another implementation, an application executing on the parent/guardian device 302 accepts input of information identifying the parent/guarding via a user interface. In yet another implementation, the parent/guardian provides cryptographic proof of identify (e.g., cryptographically signing a message with a private key known to be associated with the person, answering a cryptographic challenge issued by the server 304, etc.).

If the server 304 determines that the minor child person identified by the visual identifiers on the prescription medication container is not associated with the parent/guardian, then the server 304 transmits a message to the parent/guardian device 302 requesting permission to associate the minor child with the parent/guardian's profile (406). Associating a minor child with a parent/guardian profile allows the parent/guardian to view information regarding the status of prescriptions associated with the minor child (e.g., types of active and inactive prescriptions, prescription numbers, refill status of prescriptions, etc.) and submit requests associated therewith (e.g., refill a prescription, etc.). In this way, the parent/guardian may monitor the status of prescriptions associated with the minor child under his/her care and effectively manage the administration of the prescription medications. If the server 304 determines that the parent/guardian does not wish to associate the minor child, then the signal diagram 400 ends.

To associate a minor child with the user profile of a parent/guardian, the parent/guardian may first validate information about the minor child (408). In one implementation, information regarding the minor child is collected from the visual identifiers in the digital image(s) of the container of the prescription medication submitted by the parent/guardian and is shown to the parent guardian with a request that the parent/guardian verify the information is accurate. In another implementation, the server 304 may rely on responses input by the parent/guardian into the parent/guardian device 302 to validate against information collected from the visual identifiers in the digital image(s) of the prescription medication container. If the server 304 determines that the information provided by the parent/guardian (408) meets a validation condition, then the server 304 associates the minor child with the profile of the parent/guardian (410).

The server 304 may store information in one of the databases associated with the server 304, such as storing up-to-date information associated with patient prescriptions. Accordingly, the server 304 may use the information determined in (408) to retrieve additional information associated with the prescription from the one or more databases associated with the server 304. For example, the server 304 may retrieve, for a prescription, data indicative of remaining refills available (e.g., whether the minor child is eligible for a refill) and a preferred/default pickup location. The preferred/default pickup location may correspond to a location where the prescription was originally filled, where the prescription was last filled to a location the is determined based on GPS coordinates received from the parent/guardian device 302, to a location determined based on a zipcode or address entered by the parent/guardian into the device 302.

Figure 5:
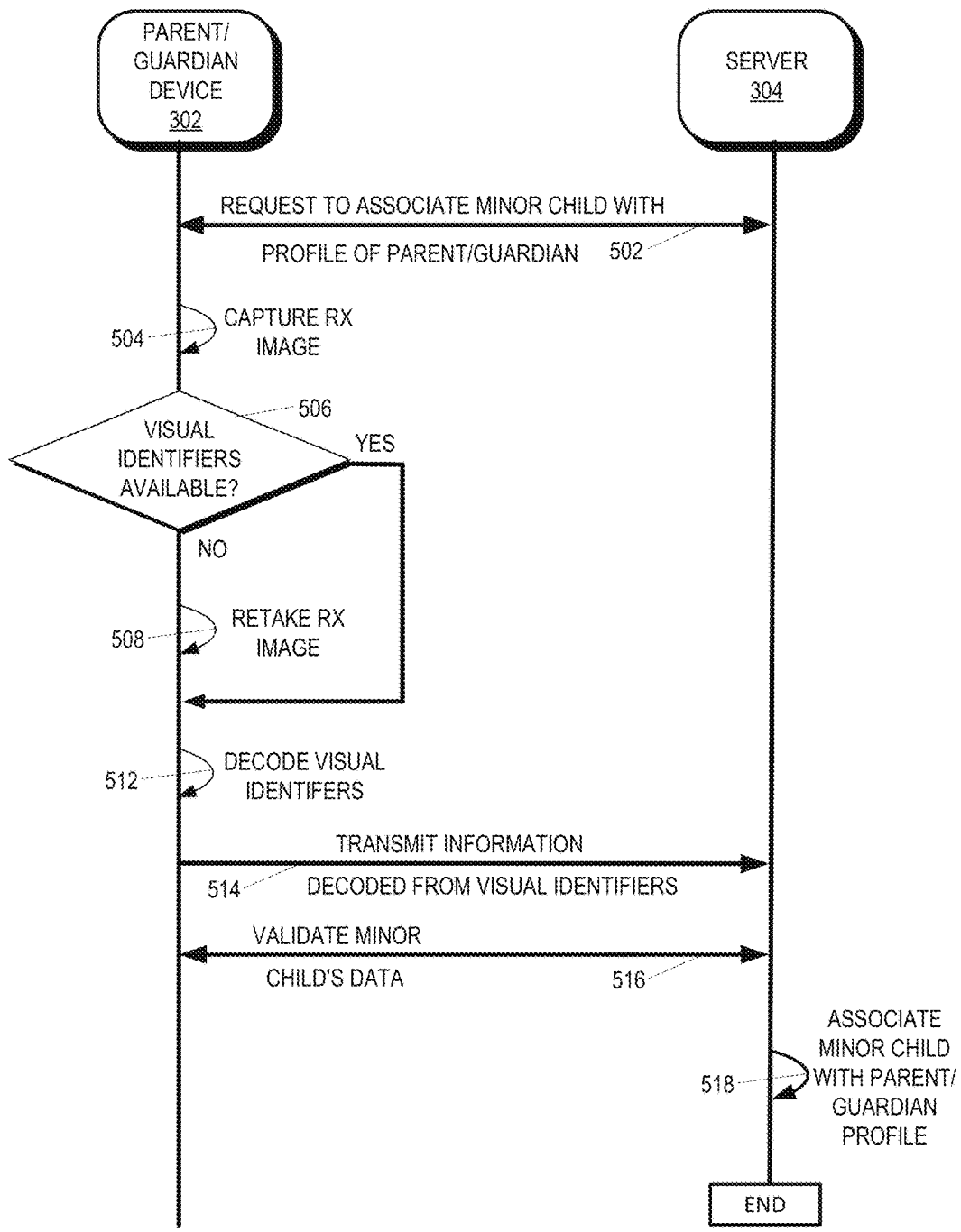
FIG. 5 is another example signal diagram associated with a system for automatic prescription processing and pharmacy profile management for minor children based on transmitted digital images.

FIG. 5 is another example signal diagram 500 associated with a system for automatic prescription processing and pharmacy profile management for minor children based on transmitted digital images. The signal diagram 500 includes a parent/guardian device 302 that may be operated by the parent/guardian of a minor child person, such as the electronic device disclosed with respect to FIG. 1, and a server 304. The server 304 may include one or more databases (e.g., a prescription information database, a user database, etc.). The server 304 may constitute a set of back-end components that are remote from the parent/guardian electronic device 302, where the set of back-end components may be associated with a pharmacy network having a set of retail locations. In another implementation, the server 304 may be associated with a single pharmacy retail location or with a third-party that does not directly operate any pharmacy locations.

The signal diagram 500 begins when a parent/guardian uses the electronic device 302 to request (502) to associate the minor child with a profile of the parent/guardian. Operation 502 may include clicking or tapping a link presented to the parent/guardian on the parent/guardian device 302 in response to an invitation from the server 304 to associate a minor child with the profile of the parent/guardian. In another implementation, operation 502 may include a request from the parent/guardian device 302 (e.g., an API request, etc.). When the server 304 receives the request in operation 502, the server may identify a parent/guardian profile of the user of the parent/guardian device 302, such as if the request in operation 502 is accompanied by or preceded by login credentials or other identification credentials (e.g., cryptographic signature, etc.)

The signal diagram 500 continues when the parent/guardian uses the electronic device 302 to capture a digital image of prescription medication information (504) such as a container associated with the prescription medication (e.g., a vial, box, tray, pill bottle, etc.). In one implementation, the container associated with a prescription medication includes a set of visual identifiers such as one or more graphical objects, logos, text, barcodes, labels, etc. The prescription medication container may include a label presenting various information associated with the prescription, including but not limited to information associated with the minor child (e.g., name, address, phone number, birthdate, etc.), dosage and usage information, and refill information. In an implementation, the parent/guardian electronic device 302 may prompt, via a user interface, the parent/guardian to capture certain portions or angles of the container. In some implementations, the parent/guardian electronic device 302 may receive or access the digital images from another device or component of the system as an alternative to directly capturing the digital image(s).

After capturing or otherwise accessing the digital image(s) (504), the parent/guardian device determines (506) whether visual identifiers are accessible in the digital image. Visual identifiers may not be accessible to the parent/guardian device 302 due to low image quality or incomplete capture of the visual identifiers in the digital image. In some implementations, the parent/guardian device 302 may employ one or more digital image analysis techniques, algorithms, routines, etc. to determine whether the visual identifiers encode prescription medication information, such as prescription medication information displayed on a prescription medication container. The parent/guardian device 302 may also employ digital image analysis techniques, algorithms, routines, etc. to assess and consider image characteristics such as sharpness, noise, range, tone reproduction, contrast, color accuracy, distortion, vignetting, exposure accuracy, lateral chromatic aberration (LCA), lens flare, color moire, and/or artifacts in the digital image(s).

If visual identifiers are not accessible in the digital image (e.g., the information contained in the visual identifiers is not decodable), the parent/guardian device 302 may request that the parent guardian retake (508) the digital image of the prescription medication information. If visual identifiers are accessible in the digital image, then the parent/guardian device 302 decodes (512) the visual identifiers to extract the information contained therein regarding the person associated with the prescription. In analyzing the visual identifiers, the parent/guardian device 302 may extract information encoded in the visual identifiers in the digital images(s). One type of information encoded in the visual identifiers in the digital image(s) is biographical information regarding the person to whom the prescription medication in the container was issued (e.g., name, address, phone number, birthdate, etc.). In at least one implementation, the container includes redundant encoding of biographical information regarding the person (e.g., human-readable text information printed on the label of the container and information encoded in a barcode printed on the container).

A transmitting operation 514 transmits the information decoded from the visual identifiers to the server 304. In another implementation, the parent/guardian device 302 may transmit the digital images of the prescription medication information itself to the server 304 via a network connection for the server 304 to decode the information in the visual identifiers. In some implementations, the parent/guardian device 302 may execute an application into which the parent/guardian may select the captured digital image(s) (e.g., from a camera roll) as well as information for the destination.

Before associating a minor child with the user profile of a parent/guardian (410), the parent/guardian may first validate information about the minor child (516). In one implementation, information regarding the minor child is collected from the visual identifiers in the digital image(s) of the container of the prescription medication submitted by the parent/guardian and is shown to the parent guardian with a request that the parent/guardian verify the information is accurate. In another implementation, the server 304 may rely on responses input by the parent/guardian into the parent/guardian device 302 to validate against information collected from the visual identifiers in the digital image(s) of the prescription medication container. If the server 304 determines that the information provided by the parent/guardian (514) meets a validation condition, then the server 304 associates the minor child with the profile of the parent/guardian (518).

Figure 6:
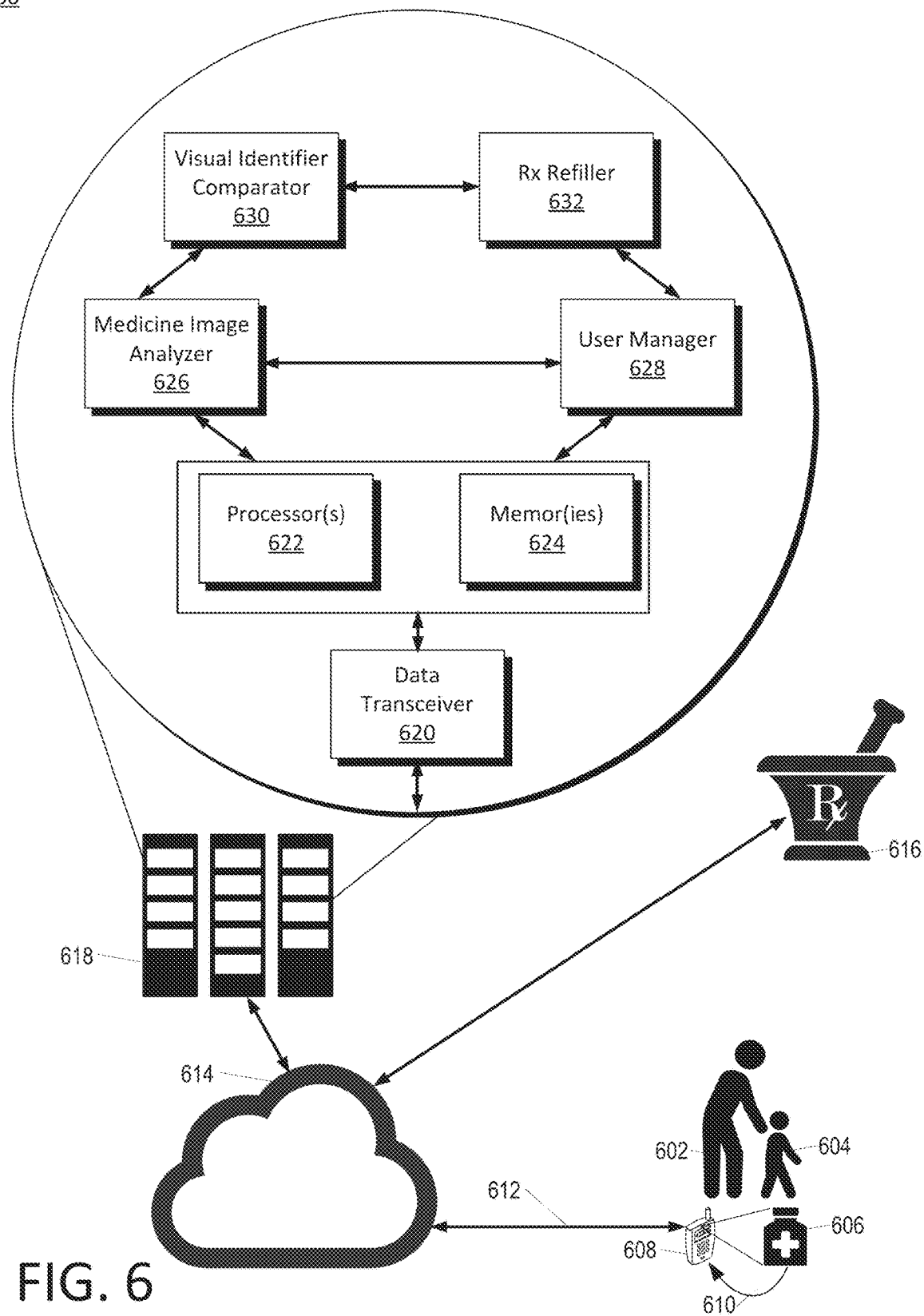
FIG. 6 is a schematic diagram of an example system for automatic prescription processing and pharmacy profile management for minor children based on transmitted digital images.

FIG. 6 is a schematic diagram of an example system 600 for automatic prescription processing and pharmacy profile management for minor children based on transmitted digital images. A parent/guardian 602 of a minor child 604 uses an electronic device 608 to capture (610) a digital image of a prescription medication container 606 or label of a prescription medication issued to the minor child 604 by a medical professional. The device 608 decodes or sends to a server 618 to decode information regarding the minor child 604 and the prescription for the medication issued in the container 606. The device 608 transmits a digital image of the container or information decided from the container to a server 618 associated with a pharmacy 616, which may be one of a network of associated pharmacies.

On the server 618, there are several components for associating a minor child 604 with a user profile of a parent/guardian 602. One component is a data transceiver 620 for sending/receiving data needed by the other components of the server 618. The server 618 includes a processor(s) 622 and memor(ies) 624. The other components of the server 618 may be implemented in hardware or software, including by instructions stored on the memor(ies) 624 and executed by the processor(s) 622. The memor(ies) 624 may include non-volatile memory storing information relied upon by the other components of server 618. For example, user profiles, prescription information, pharmacy information, etc. may be stored on memor(ies) 624.

The server 618 includes a medicine image analyzer 626 configured to detect visual identifiers in a digital image of the prescription medication container 606 or another source of information regarding a prescription (e.g., a prescription label). The medicine image analyzer detects visual identifiers that encode information regarding the minor child 604 and/or a prescription for medication issued to the minor child (e.g., barcodes, text, symbols, etc.). In an implementation, a visual identifier comparator correlates or decodes visual identifiers to extract information contained therein. For example the visual identifier comparator 630 may decode barcodes identified by the medicine image analyzer 626 or apply OCR techniques to extract textual information printed on the prescription medication container 606.

A user manager 628 locates user information regarding the parent/guardian and the minor child 604. In one implementation, the user manager includes a user profile data stored on the memor(ies) 624 to locate and edit user profiles belonging to the parent/guardian. The user manager 628 may query the parent/guardian to validate biographical information of the minor child 604 via the network 614. If the parent/guardian response to a validation query satisfies a validation condition, the user manager 628 may associate the minor child 604 with an profile of the parent/guardian. Once associated, the parent/guardian 602 may request information or submit requests to the server 618 to the user manager 628 to manage other prescriptions issued to the minor child 604.

One type of request that the parent/guardian 602 may submit to the user manager 628 is a request to refill a prescription medication issued to the minor child 604. The parent/guardian 602 may, via the device 608, submit a request to the prescription refiller 632 a request to fill a prescription at a pharmacy location 616. The prescription refiller 632 may transmit refill instruction to the pharmacy 616 if the user manager 628 determines that the prescription is valid, has at least one refill remaining, and the minor child 604 is associated with a profile of the parent/guardian 602.

Figure 7:
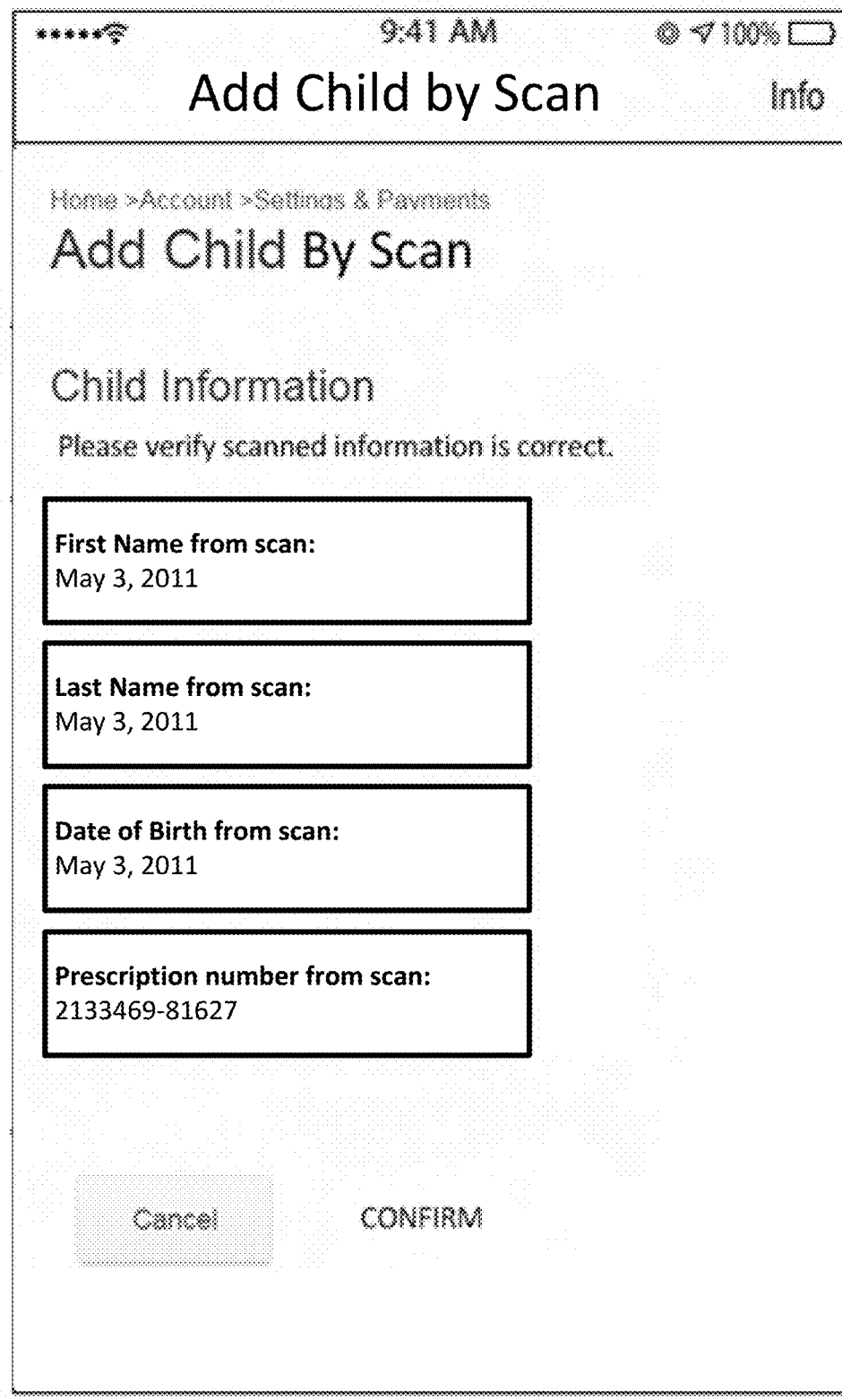
FIG. 7 is an example user interface associated with a system for automatic prescription processing and pharmacy profile management for minor children based on transmitted digital images.

FIG. 7 is an example user interface screen 700 associated with a system for automatic prescription processing and pharmacy profile management for minor children based on transmitted digital images. In an implementation, the user interface screen 700 is displayed on an electronic device used by a parent/guardian of a minor child. The screen 700 illustrates a verification screen displayed to a parent/guardian before associating the minor child with a user profile of the parent/guardian. In one implementation, the information regarding the minor child on screen 700 is shown based on a decoding of visual identifiers in a digital image captured by an electronic device of the parent/guardian.

Figure 8:
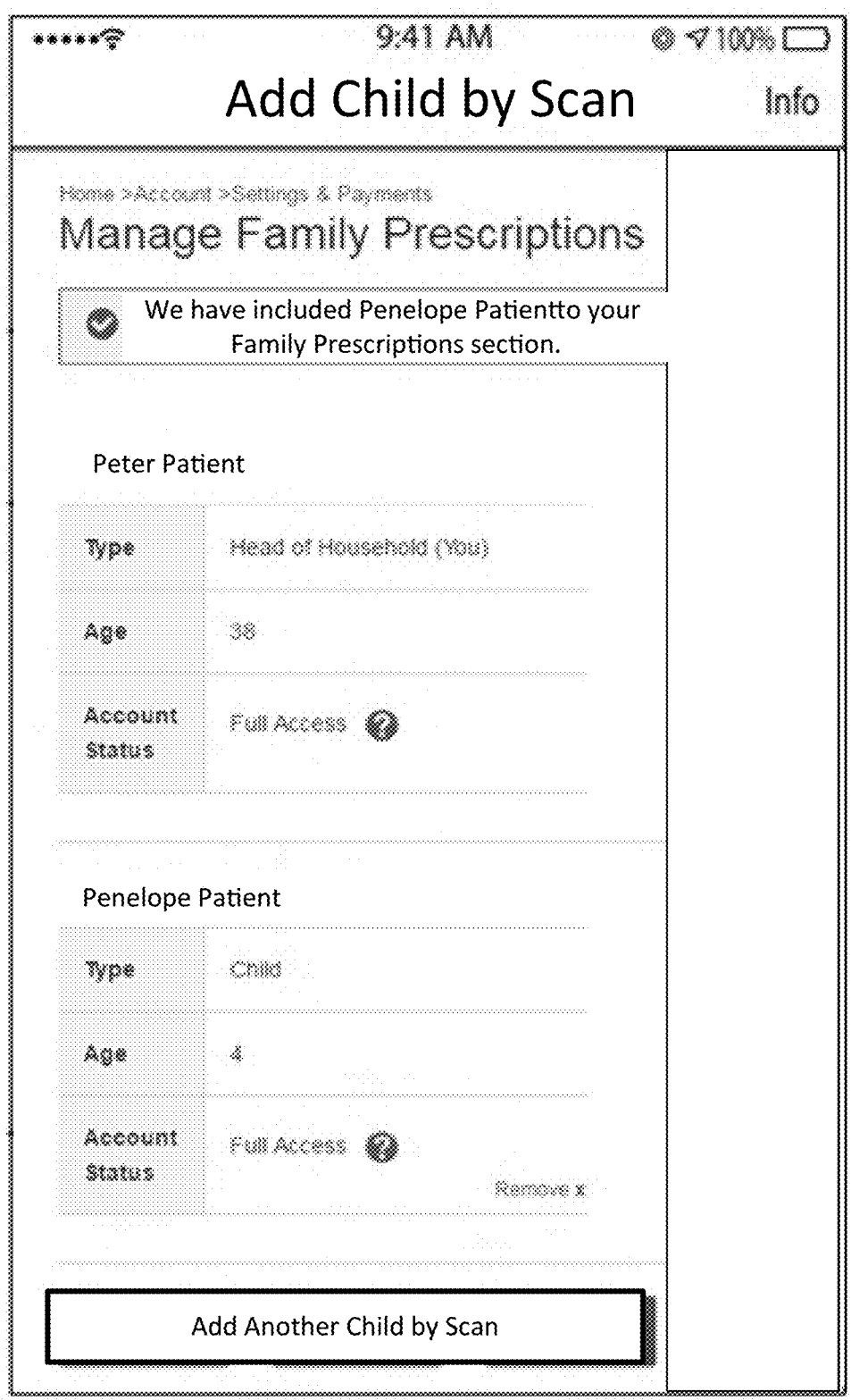
FIG. 8 is an example user interface associated with a system for automatic prescription processing and profile management for minor children based on transmitted digital images.

FIG. 8 is an example user interface screen 800 associated with a system for automatic prescription processing and pharmacy profile management for minor children based on transmitted digital images. The user interface screen 800 illustrates how a parent/guardian may access information relating to a minor child in a user profile. In addition to the information displayed in screen 800, a parent/guardian may access information relating to any prescriptions filled or refilled by the parent/guardian on behalf of a minor child in the past and the ability to submit requests for the refill and/or transfer of prescriptions on behalf of the minor child.

Figure 9:
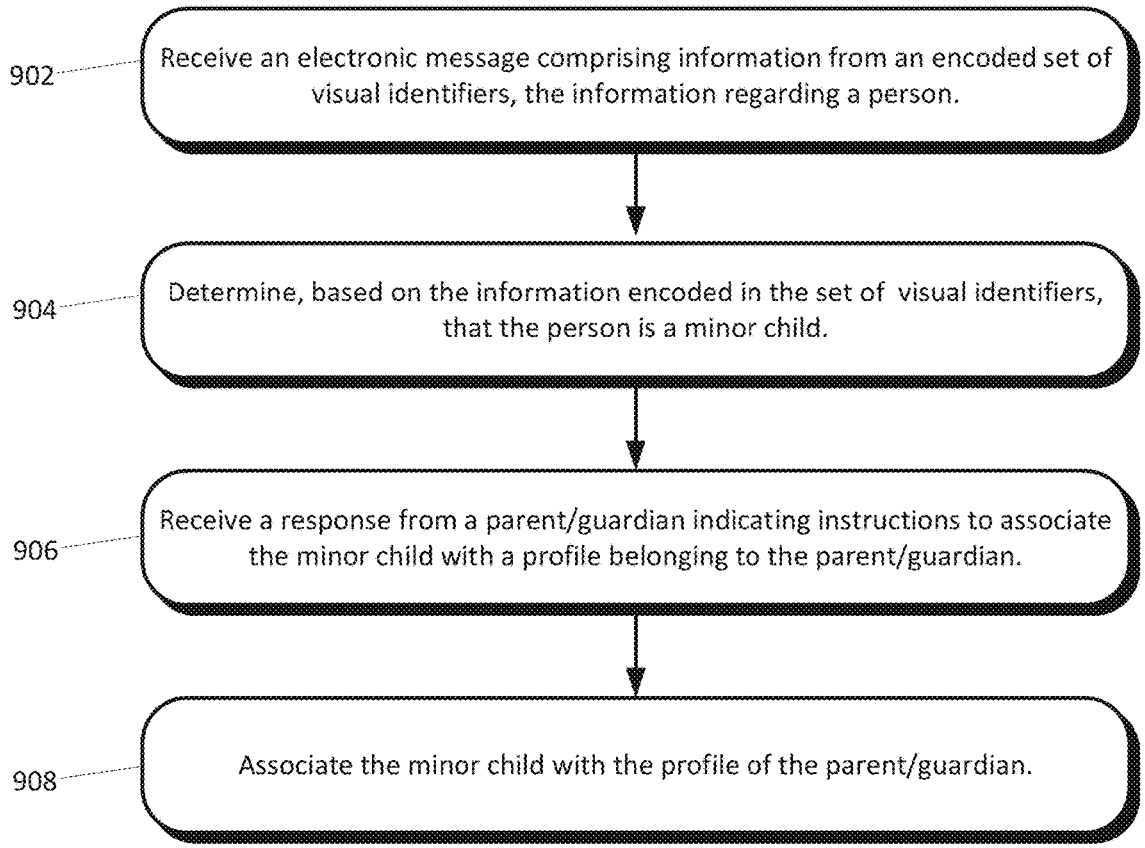
FIG. 9 illustrates example operations for automatic prescription processing and profile management for minor children based on transmitted digital images.

FIG. 9 illustrates example operations 900 for automatic medication processing and pharmacy profile management for minor children based on transmitted digital images. A receiving operation 902 receives an electronic message including prescription medication information from an encoded set of visual identifiers captured in a digital image of prescription information. A server may perform the receiving operation 902 by receiving a digital image from an electronic device used by a parent/guardian.

A determining operation 904 determines, based on the information encoded in the set of visual identifiers, that the person is a minor child. In one implementation, the determining operation 904 calculates an age of the person based on a birthdate encoded in the visual identifiers. A receiving operation 906 receives a response from a parent/guardian instructions to associate the minor child with a profile belonging to the parent/guardian. In one implementation, the user profile is a user profile at a network pharmacy. In another implementation, the instructions in receiving operation 906 include a validation of biographical information of the minor child. An associating operation 908 associates the minor child with an profile of the parent/guardian (e.g., a customer of the pharmacy).

Of course, the applications and benefits of the systems, methods and techniques described herein are not limited to only the above examples. Many other applications and benefits are possible by using the systems, methods and techniques described herein.

Furthermore, when implemented, any of the methods and techniques described herein or portions thereof may be performed by executing software stored in one or more non-transitory, tangible, computer readable storage media or memories such as magnetic disks, laser disks, optical discs, semiconductor memories, biological memories, other memory devices, or other storage media, in a RAM or ROM of a computer or processor, etc.

What is claimed:

1. A method of processing medication refills, the method comprising:

receiving, at one or more servers associated with a pharmacy network, an electronic message originating from an electronic device of a user, the electronic message comprising information from an encoded set of visual identifiers from a digital image of medication information from a medical prescription container of a patient, and the one or more servers storing a profile of the user and a profile of the patient;

determining, by the one or more servers and based on the information encoded in the set of visual identifiers, that the patient is under a legal guardianship;

determining, by the one or more servers, that the user profile stored at the one or more servers is unassociated with the patient profile stored at the one or more servers with regard to management of prescriptions of the patient;

receiving, at the one or more servers, a response from the user, the response indicating user instructions to associate the patient profile stored at the one or more servers with the user profile stored at the one or more servers for prescription management of the patient;

determining, by the one or more servers, that the user is authorized to manage prescriptions on behalf of the patient;

based upon the determination that the user is authorized to manage prescriptions on behalf of the patient, storing, at the one or more servers, an indication of an association of the patient profile and the user profile corresponding to prescription management of the patient, thereby allowing the user to manage prescriptions on behalf of the patient via the pharmacy network; and causing a prescription of the patient to be dispensed based upon the stored indication of the association between the patient profile and the user profile corresponding to prescription management of the patient.

2. The method of claim 1, further comprising determining, based on the set of visual identifiers, that the patient has at least one prescription associated with a pharmacy associated with the pharmacy network.

3. The method of claim 1, wherein causing the prescription of the patient to be dispensed includes transmitting refill instructions to a pharmacy associated with the pharmacy network.

4. The method of claim 1, wherein the user is a legal guardian of the patient.

5. The method of claim 1, further comprising enabling, based on the stored association, the user to view information regarding medications of the patient that are not identified by the digital image of medication information.

6. The method of claim 1, wherein receiving the response from the user includes receiving validation information corresponding to the patient being under the legal guardianship.

7. The method of claim 1, wherein receiving the electronic message includes receiving the digital image including the set of visual identifiers.

8. A system for prescription request processing and prescription management for patients under legal guardianship, the system comprising:
one or more memories storing profiles of persons with whom one or more pharmacies has had interactions, the profiles including a profile of a user and a profile of a second person;
a network connection via which the system receives, via one or more networks, an electronic message originating from an electronic device associated with the user, the electronic message comprising information encoded in a set of visual identifiers captured in a digital image corresponding to a medical prescription of the second person;
a visual identifier comparator comprising a first set of instructions stored on the one or more memories and executable by one or more processors of the system to determine, based on the information encoded in the set of visual identifiers, that the second person is under a legal guardianship; and a user manager comprising a second set of instructions stored on the one or more memories and executable by the one or more processors of the system to:
determine, based on the information encoded in the set of visual identifiers, that an indication of the profile of the user being associated with the profile of the second person for prescription management of the second person is not stored in the one or more memories;
based on the determination that the indication of the profile of the user being associated with the profile of the second person for prescription management of the second person is not stored in the one or more memories, determine that the user is authorized to manage prescriptions on behalf of the second person, including receiving instructions from the user to associate the profile do the second person with the profile of the user for prescription management of the second person; and
based on the determination that the user is authorized to manage prescriptions on behalf of the second person:
storing, in the one or more memories, the indication of the profile of the user being associated with the profile of the second person for prescription management of the second person, thereby allowing the user to manage prescriptions on behalf of the second person via the system; and
causing the medical prescription or another medical prescription of the second person to be dispensed.

9. The system of claim 8, wherein the second set of instructions of the user manager is further executable to determine whether or not the user has a user profile associated with a pharmacy included in the one or more pharmacies.

10. The system of claim 9, further comprising:
a medication refiller comprising a third set of instructions stored on the one or more memories and executable by the one or more processors to transmit a medication refill request for the medical prescription to the pharmacy.

11. The system of claim 8, wherein the electronic message comprises a digital image of medication information depicted on a medication container corresponding to the medical prescription.

12. The system of claim 8, wherein the first set of instructions of the visual identifier comparator is further executable to determine, based on the set of visual identifiers, that the second person is a minor child by comparing a birth date indicated by the set of visual identifiers with a current date.

13. The system of claim 10, wherein the third set of instructions of the medication refiller is further executable to transmit a medication transfer request to another pharmacy included in the one or more pharmacies.

14. The system of claim 8, wherein the second set of instructions of the user manager is further executable to approve validation information regarding the second person.

15. A method of processing medication transfers for a patient, the method comprising:
receiving, at one or more servers associated with a pharmacy, an electronic message originating from an electronic device of a user, the electronic message including a digital image including a plurality of visual identifiers and corresponding to a medication prescription container of the patient, and the one or more servers storing a profile of the user and a profile of the patient;

detecting, by the one or more servers, a set of visual identifiers of the plurality of visual identifiers depicted in the digital image, the set of visual identifiers encoding information regarding the patient;

decoding, by the one or more servers, medication information in the set of visual identifiers;

determining, by the one or more servers and based on the medication information, that the patient is under a legal guardianship;

determining, by the one or more servers, that the user profile stored at the one or more servers is unassociated with the patient profile stored at the one or more servers with regard to prescription management of the patient;

receiving, at the one or more servers, a response from the user, the response indicating user instructions to associate the patient profile stored at the one or more servers with the user profile stored at the one or more servers with regard to prescription management of the patient;

determining, by the one or more servers, that the user is authorized to manage prescriptions on behalf of the patient; and based on the determination that the user is authorized to manage prescriptions on behalf of the patient:

storing, at the one or more servers, an association of the patient profile and the user profile with regard to prescription management of the patient, thereby allowing the user to manage prescriptions on behalf of the patient via the one or more servers associated with the pharmacy; and causing a prescription of the patient to be dispensed.

16. The method of claim 15, wherein the user is a legal guardian of the patient.

17. The method of claim 15, wherein the digital image originating from the electronic device depicts the medication prescription container of the patient.

18. The method of claim 15, wherein receiving response from the user indicating the user instructions includes receiving validation information corresponding to the patient being under the legal guardianship.

19. The method of claim 18, wherein the validation information includes a birthdate of the patient.

20. The method of claim 15, further comprising:

receiving, by the one or more servers, a request of the user to refill the prescription or another prescription for the patient.

* * * * *